United States Patent
Uhen

[11] Patent Number: 5,386,833
[45] Date of Patent: Feb. 7, 1995

[54] METHOD FOR CALIBRATING A CARBON DIOXIDE MONITOR

[75] Inventor: David Uhen, Burlington, Wis.

[73] Assignee: Biochem International, Inc., Waukesha, Wis.

[21] Appl. No.: 173,522

[22] Filed: Dec. 23, 1993

[51] Int. Cl.[6] .............................................. A61B 5/08
[52] U.S. Cl. ................................. 128/719; 128/725; 73/23.3
[58] Field of Search ............... 128/716, 719, 725, 718, 128/724, 720; 73/23.3

[56] References Cited

U.S. PATENT DOCUMENTS

| | | |
|---|---|---|
| 4,578,762 | 3/1986 | Wong .................................. 128/719 |
| 5,060,656 | 10/1991 | Howard ............................. 128/719 |

*Primary Examiner*—William E. Kamm
*Assistant Examiner*—Brian M. Grew
*Attorney, Agent, or Firm*—Quarles & Brady

[57] ABSTRACT

An apparatus periodically measures the carbon dioxide content of the breath of a medical patient. The need to recalibrate the apparatus is determined by comparing the carbon dioxide measurements taken at different times during the respiratory cycle to corresponding reference levels. These levels often occur when the apparatus no longer is measuring accurately. When recalibration is indicated the apparatus waits until the patient begins inhaling so that the recalibration does not interfere with measuring the carbon dioxide during exhalation. The apparatus then measures the carbon dioxide content of the ambient air to define an offset value used in patient monitoring.

21 Claims, 4 Drawing Sheets

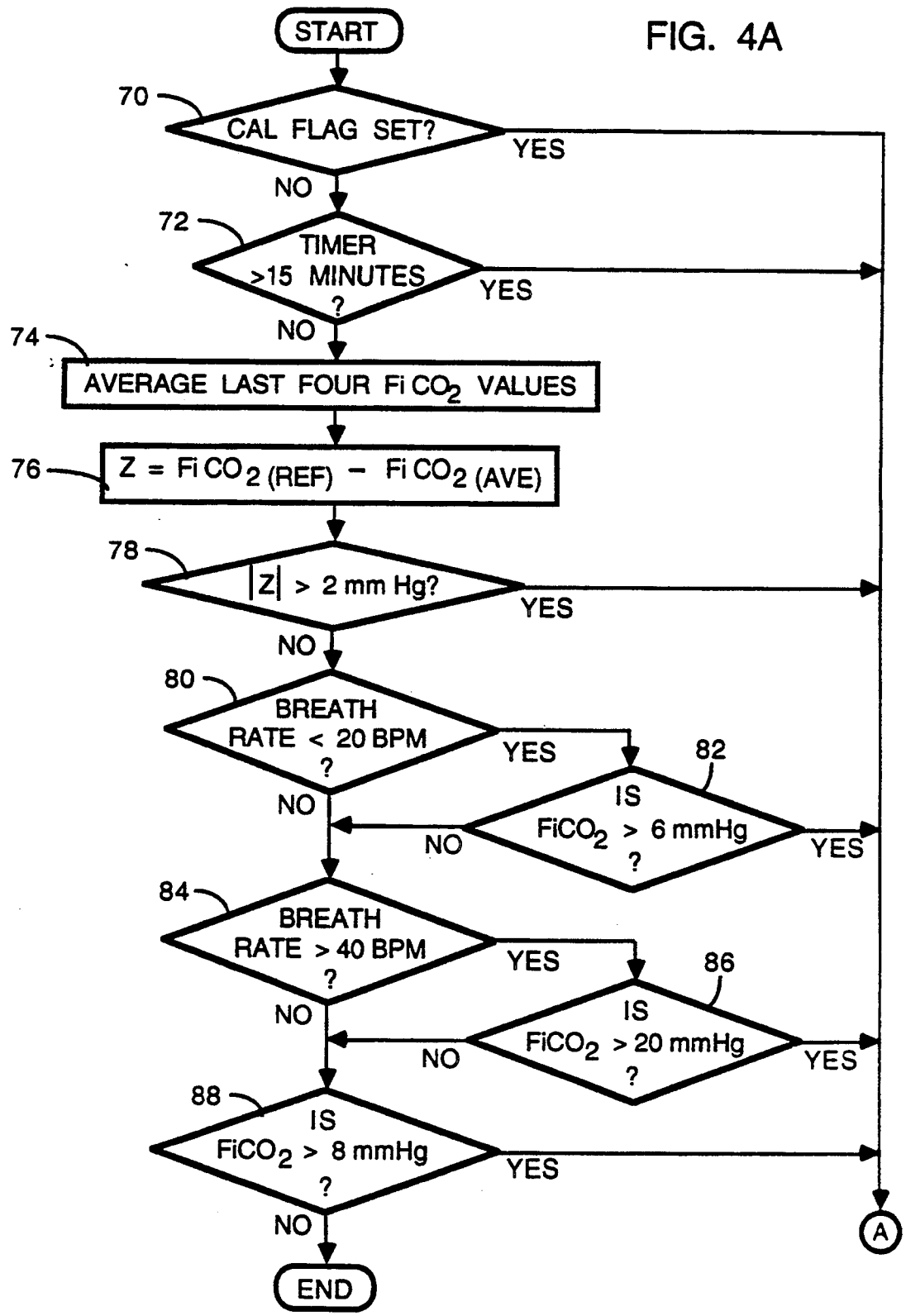

METHOD FOR CALIBRATING A CARBON DIOXIDE MONITOR

BACKGROUND OF THE INVENTION

The present invention relates to devices for monitoring the carbon dioxide content in air being exhaled by a medical patient, and more particularly to techniques for calibrating such monitoring devices.

Medical patient connected to a respirator typically have the carbon dioxide ($CO_2$) content of their exhaled air monitored. The carbon dioxide content was conventionally measured as a partial pressure, expressed in terms of millimeters of mercury. Heretofore, devices that performed such monitoring are relatively large, table model units which were not easily transported and which were used in the relatively controlled environment of a hospital.

Recently, a hand-held carbon dioxide monitor has been developed which offers several advantages over previous table model units. The hand-held device can easily be carried from patient to patient in an intensive care unit so that a single device can be connected alternately to the respirators for a number of patients. Thus, a single unit can be used to monitor the amount of carbon dioxide exhaled by several patients as opposed to requiring a separate table model unit for each patient. In addition, the hand-held unit can be transported in an ambulance and used by paramedics following resuscitation of accident victims.

Previous carbon dioxide monitors had to be calibrated periodically to compensate for changes in the performance of components with age and temperature fluctuation. Typically the carbon dioxide monitor executed a calibration procedure when power was first applied. In addition, during prolonged continuous use of the monitor, an internal timer periodically triggered recalibration.

During the development of a hand-held carbon dioxide monitor, it was discovered that such devices were subjected to mechanical shock during transportation. In addition, the use in ambulances subjected the monitor to rapid changes in temperature. The affects of such mechanical shock and temperature variation during periods of non-use, such as when the device is being transported to a patient, can easily be compensated for by executing the calibration routine during initial power-up of the monitor. However, the use of monitors connected to accident victims also subject the monitor to mechanical shock and temperature variation as the patient is transported from the accident scene to an ambulance and then from the ambulance to a hospital emergency room. Therefore, the accuracy of the hand-held carbon dioxide monitor drift during even short periods of operation.

SUMMARY OF THE INVENTION

An object of the present invention is to provide a mechanism for determining when calibration is necessary during the operation of a carbon dioxide monitor.

Another object of the present invention is to determine when calibration is required based on an analysis of the carbon dioxide measurements taken of a patient.

The monitoring device periodically measures the carbon dioxide content of air being breathed by the animal. The carbon dioxide measurements are analyzed to determine when the accuracy of the device begins to drift to a degree that recalibration is required. Preferably, the recalibration takes place during inhalation of the animal so as not to interfere with continued monitoring of the carbon dioxide in air being exhaled by the animal. However, if the device detects that the animal is in apnea the recalibration begins immediately.

In the preferred embodiment a plurality of analytical tests are performed on the carbon dioxide measurements to detect a need for recalibration. These tests include determining when:

(a) a difference between an average of the fractional inspired carbon dioxide level during a plurality respiratory cycles and a reference level exceeds a given threshold, (b) the number of measurements of the relative carbon dioxide content of the patient's breath that have a negative value exceeds a predefined value, (c) the number of measurements of the carbon dioxide content that are above a threshold level, during apnea, exceeds a predetermined value, and (d) the fractional inspired carbon dioxide is greater than a predefined level when the breath rate of the animal is below a predetermined level.

Any one or a combination of one or more of these analytical tests can be used by the carbon dioxide monitoring device to determine when recalibration is necessary.

The recalibration procedure involves measuring the carbon dioxide content of the ambient air surrounding the device. A zero carbon dioxide reference level is defined using the carbon dioxide content of ambient air. Subsequent measurements of the carbon dioxide exhaled by the animal are relative to the newly defined zero carbon dioxide reference level.

BRIEF DESCRIPTION OF THE DRAWINGS

FIGS. 4A and 4B are a flowchart of a software routine which calibrates the carbon monoxide monitor.

DETAILED DESCRIPTION OF THE INVENTION

Figure 1:
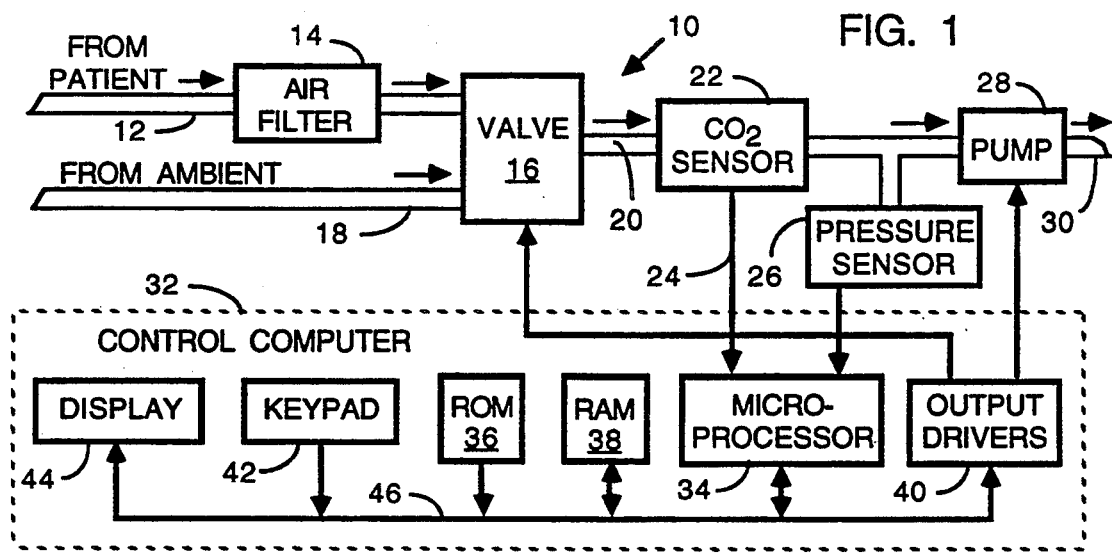
FIG. 1 is a block diagram of a hand-held carbon dioxide monitor incorporating the present invention.

With initial reference to FIG. 1, a hand-held carbon dioxide monitor 10 has a tube 12 connected to a respirator to receive air that is being inhaled and exhaled from a medical patient. That received air passes through filter 14 which is connected to one input of a valve 16 and another input of the valve is connected to a tube 18 which receives air from the ambient atmosphere of the monitor 10. Valve 16 is electrically controlled and connects one of the two inputs to an output tube 20.

The air passing through the valve 16 enters a standard carbon dioxide ($CO_2$) sensor 22 having a chamber through which the air flows. A light beam is sent through the chamber at a specific wavelength which is affected by the carbon dioxide in the gas. A detector senses the amount of light passing through the chamber and produces an electrical signal on output lines 24 that is indicative of the amount of carbon dioxide in the sensing chamber. This type of carbon dioxide sensor is well-known and one suitable model is manufactured by Sensors, Inc. Although this type of carbon dioxide sensor is relatively accurate, its accuracy is dependent upon a number of factors, such as the temperature of the device, the changes in performance of the light source and detector with age, and the sensor is sensitive to mechanical shock which may cause a sudden shift in the measurements. The sensor 22 has an integral temperature transducer that produces an electrical signal on cable 24 which indicates the temperature of the sensor, thereby enabling the electronics in the monitor 10 to compensate for temperature variations which affect the carbon dioxide measurement.

An output port of the carbon dioxide sensor 22 is coupled to a pressure transducer 26 which senses the pressure of the air flowing through the monitor and allows the amount of carbon dioxide to be expressed as a partial pressure, the accepted manner of expression in the medical field. The output port of the $CO_2$ sensor 22 also is connected to an electrically operated pump 28 which draws air through the monitor from either tube 12 or tube 18 as selected by valve 16 and exhausts the air through an outlet port 30 into the ambient environment.

The carbon dioxide monitor 10 includes a control computer 32 which, in addition to processing the output from the $CO_2$ sensor 22, controls the operation of other components of the hand-held monitor. The output signals from sensor 22 representing the carbon dioxide content of the air and the temperature of the sensor are connected to inputs of a microprocessor 34 within computer 32. The output signal from the pressure sensor 26 is connected to another input of the microprocessor 34. The microprocessor 34 executes a program that is stored in a read only memory (ROM) 36 and data used or produced by the microprocessor are stored in a random access memory (RAM) 36. During the execution of the program, the microprocessor sends control signals to a set of output drivers 40 which respond by activating the valve 16 and pump 28.

The user controls the carbon dioxide monitor and selects various operating modes via a keypad 42 which is part of the control computer 32. The results of the processing, such as the patient's breath rate and measured carbon dioxide are presented to the user on a display unit 44 which also displays other operating information about the monitor. Components 34, 36, 38, 40, 42 and 44 are connected together by a set of buses 46 which contain conductors for data, address and control signals.

Figure 2:
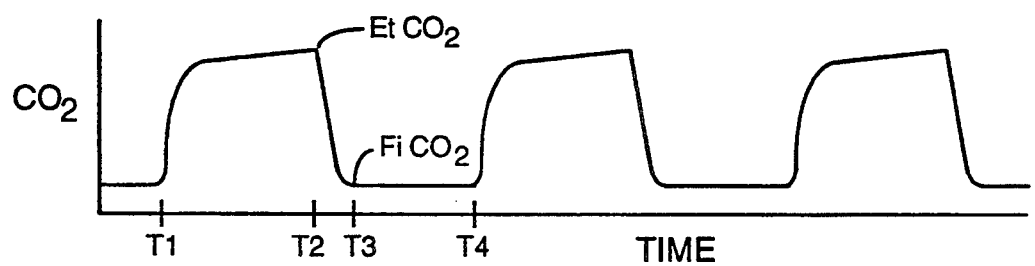
FIG. 2 is a graph of the carbon monoxide measurements of a patient during several respiratory cycles.

The hand-held monitor 10 senses the carbon dioxide content of the patient' breath periodically during each respiration cycle. FIG. 2 graphically depicts the patient's carbon dioxide level during three respiration cycles. The carbon dioxide in the air flowing through the patient's respirator rises rapidly at time T1 as the patient begins to exhale and then rises more slowly as air deeper inside the patient's lungs is exhaled. At the end of the exhalation portion of the respiratory cycle (time T2), the end tidal carbon dioxide (Et $CO_2$) level occurs, which is the carbon dioxide level displayed by monitor 10.

Thereafter, the patient begins to inhale and the carbon dioxide content in the patient's air flow drops dramatically because the ambient air with a relatively low carbon dioxide content is being drawn into the respirator. The inhalation portion of the respiratory cycle occurs between times T2 and T4, after which the patient exhales again. The carbon dioxide value at time T3, when the slope of the waveform reaches zero, is known as the fractional inspired carbon dioxide measurement (Fi $CO_2$) and typically is the lowest value which occurs during the respiratory cycle. Note that the measured carbon dioxide level does not necessarily drop to zero during the respiration cycles depicted in FIG. 2. The zero carbon dioxide level on the graph represents the amount of carbon dioxide in the ambient air measured by the monitor 10 during the calibration procedure. The carbon dioxide content of the patient's breath is measured in relation to the ambient carbon dioxide level.

The program stored in ROM 36, which the control computer 32 executes, digitally samples the signal from the carbon dioxide sensor 22 thirty times a second and stores the samples in a section of RAM 38. The monitor 10 employs a technique similar to that used in previous carbon dioxide monitors to convert the sensor signal sample into a carbon dioxide measurement. The measurements of the carbon dioxide in the patient's breath are with reference to the amount of carbon dioxide in the ambient air and are displayed as a partial pressure in units of millimeters of mercury. Conventional techniques also are employed to detect the measurements that correspond to the end tidal carbon dioxide value (Et $CO_2$) and the fractional inspired carbon dioxide value (Fi $CO_2$), which values are stored in RAM 38.

Figure 3:
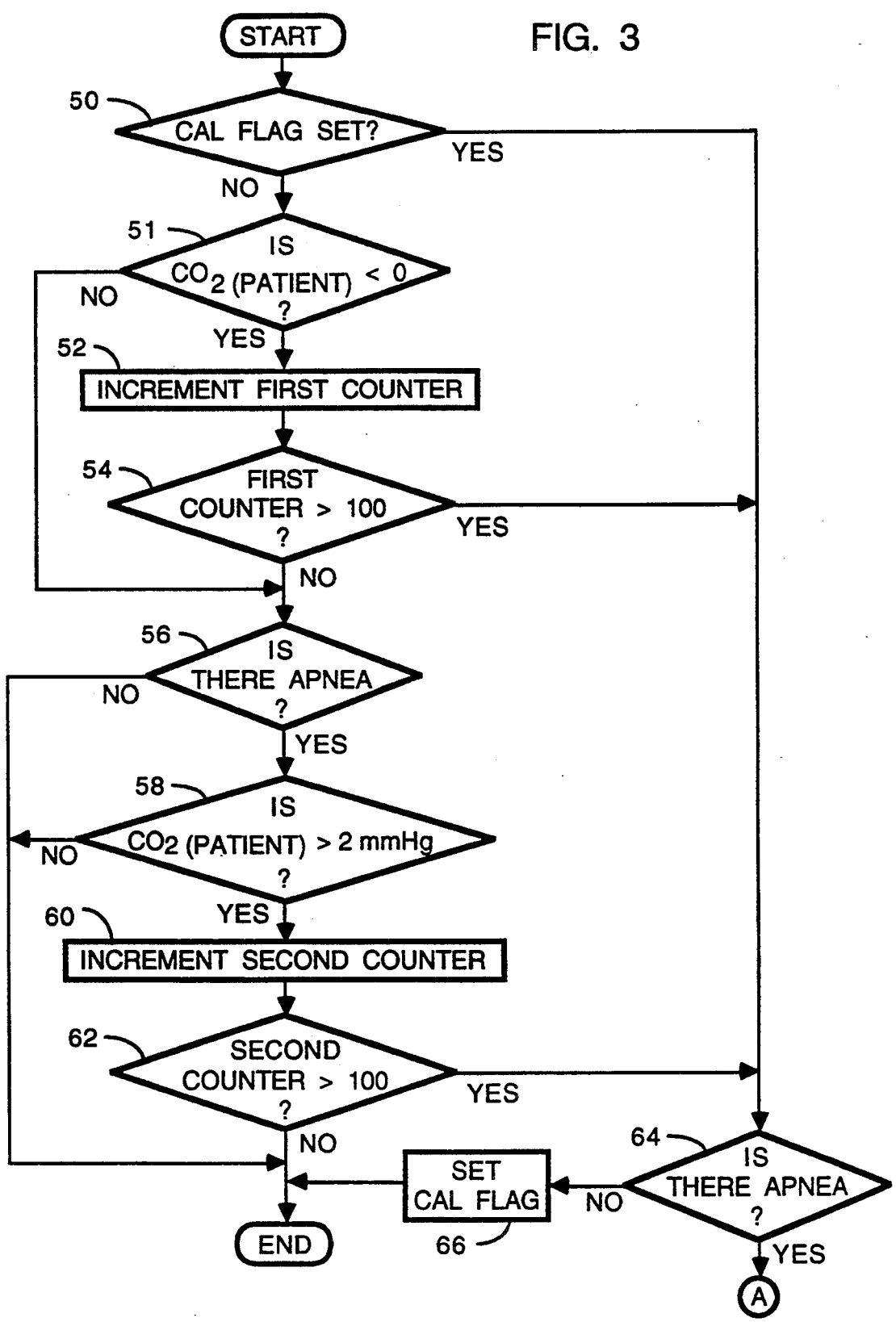
FIG. 3 is a flowchart of a software routine that evaluates measurements of carbon dioxide to determine whether the monitor requires recalibration.

As noted previously, a number of environmental factors can cause a drift in the accuracy of the hand-held carbon dioxide monitor 10. Thus, after each signal sample is acquired from the sensor 22 and converted into a carbon dioxide measurement, microprocessor 34 executes a routine that evaluates the measured value to determine if recalibration is warranted. The measurement evaluation routine, which is stored as part of the program within ROM 36, is depicted in FIG. 3 and commences at step 50 where the microprocessor checks a flag, designated CAL FLAG, that indicates when a previous determination was made that the monitor requires recalibration. As will be described, the recalibration procedure often in delayed until the patient is inhaling to reduce interference with carbon dioxide measurements during exhalation which are of primary interest. If at step 50 the CAL FLAG is found to be set, the program execution branches to step 64.

Otherwise the program advances to step 51 where the recently acquired carbon dioxide measurement is evaluated. The zero carbon dioxide level in FIG. 2 is the amount of carbon dioxide present in the ambient air and the content of the carbon dioxide in the patient's air is considered to be the amount in excess of the ambient carbon dioxide content. Occasionally during normal operation of the monitor, the measured carbon dioxide will be less than this zero level. However, the measured carbon dioxide amount going below the zero level (i.e. a negative carbon dioxide measurement) too frequently indicates that the accuracy of monitor 10 has shifted and recalibration is necessary. Thus at step 51 a determination is made whether the relative amount of carbon dioxide measured from the patient is less than zero, in which case a first counter is incremented at step 52. Then at step 54, a determination is made whether the first counter has a count that is greater than 100. When this occurs, calibration is indicated and the program execution branches to step 64. Other software for the monitor 10 provides a timed interrupt of the microprocessor 34 which decrements the first counter by one every second to compensate for normal occurrences of the measured carbon dioxide dropping below the level in the ambient air. Thus, the monitor 10 will be recalibrated, if in spite of periodic decrementing, the count maintained by the first counter exceeds 100 at step 54.

If either the carbon dioxide measurement is not less than zero as determined at step 51 or the first counter has not reached 100 at step 54, the program execution advances to step 56 where a determination is made whether the patient is in apnea. The main program executed by the microprocessor 34 calculates the breathing rate by counting the number of respiration cycles occurring within a given period of time. If no breath occurs for 30 seconds, the microprocessor 34 concludes that the patient is in apnea and sets an apnea flag. If at step 56 the apnea flag is set, the measured carbon dioxide level should be very close to zero, since air is not being exhaled from a patient. Therefore, a determination is made at step 58 during apnea whether the carbon dioxide partial pressure measurement is greater than two millimeters of mercury, a level that should not occur during apnea. If that level is exceeded, a second counter is incremented at step 60. The timed interrupt which decrements the first counter also decrements the second counter by one every second. However, neither counter can be decremented below zero. At step 62, the microprocessor determines whether the count in the second counter is greater than 100, which indicates that the accuracy of the monitor 10 has changed and offset calibration should be performed. In such a case, the program execution branches from step 62 to step 64. Otherwise, the measurement evaluation routine ends by returning to the main program.

When recalibration in indicated, a determination is made at step 64 whether the patient is in apnea, as denoted by the apnea flag. If apnea exists based on the criteria used at step 56, the offset calibration routine commences immediately by jumping to step 90. Otherwise, the recalibration is delayed until the patient is in the inhalation portion of the respiration cycle so that the monitor 10 will not skip any measurements of the end tidal carbon dioxide content. Therefore, when apnea is not occurring, the program execution branches to step 66 where the CAL FLAG is set to indicate that calibration should occur after the next measurement of Fi $CO_2$. The routine then returns to the main program. Thus, the recalibration is synchronized to the patient's respiration, occurring between times T3 and T4 while the patient is inhaling.

Figure 4B:
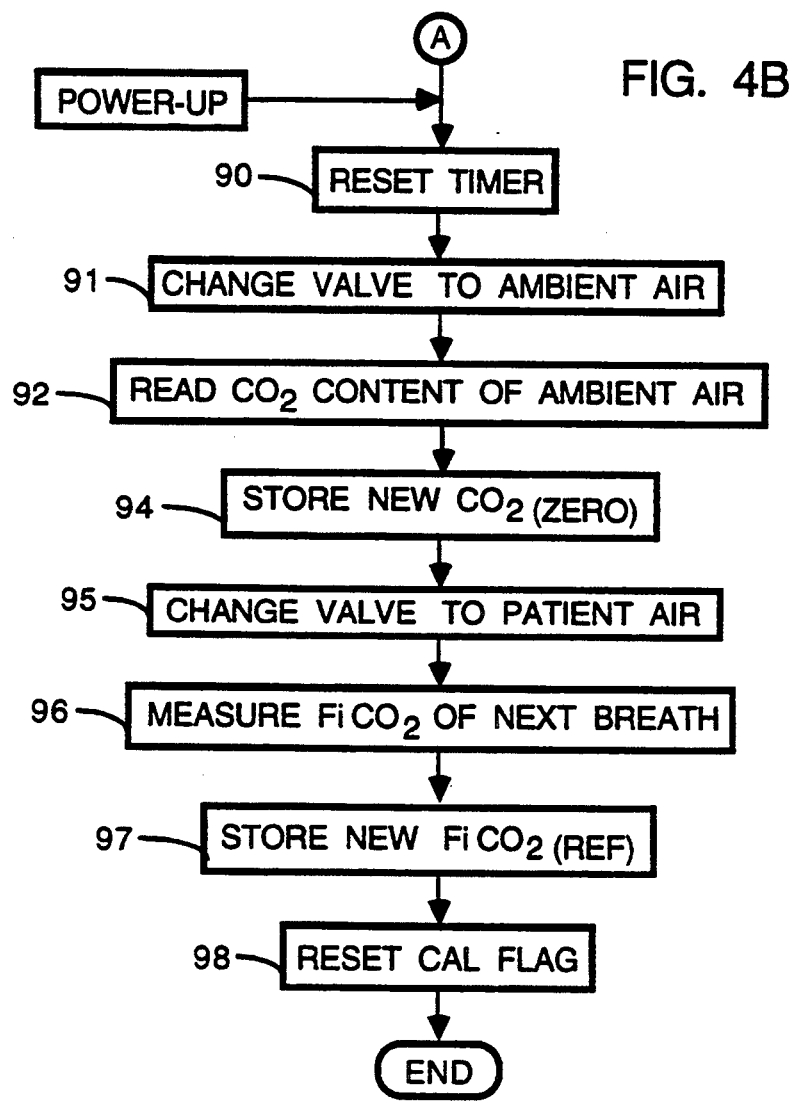

After the control computer 32 acquires the fractional inspired carbon dioxide measurement at time T3 during each respiration cycle, the microprocessor 34 calls an routine which evaluates that measurement to determine whether calibration is indicated. With reference to FIG. 4A, this routine commences at step 70 where the microprocessor 34 checks the CAL FLAG and if that flag is set the program execution jumps to step 90 on FIG. 4B where the offset calibration procedure begins.

Otherwise, the program execution advances to step 72 where a timer that is maintained by the microprocessor 34 is checked. If the timer indicates that fifteen minutes have elapsed since the previous calibration of the monitor 10, the program execution jumps to step 90 at the beginning of the offset calibration procedure depicted in FIG. 4B. Thus, even if none of the other factors indicates that calibration is required, the hand-held monitor 10 is recalibrated automatically every fifteen minutes during continuous operation.

A need to recalibrate the carbon dioxide monitor 10 is indicated when the level of the fractional inspired carbon dioxide (Fi $CO_2$) begins drifting. In theory, this level should be constant for a given patient and a drift in the measurement may indicate that the accuracy of the carbon dioxide sensor 22 or other components of the system has changed. To detect such drift, the microprocessor 34 at step 74 averages the four most recent measurements of the fraction inspired carbon dioxide, the values of which were stored in RAM 38 for this averaging process. As will be described, the first fractional inspired value measured after each calibration of the monitor 10 is stored as a reference measurement of the fractional inspired carbon dioxide, Fi $CO_{2\ (REF)}$. At step 76, the average fractional inspired carbon dioxide Fi $CO_{2\ (AVE)}$ is subtracted from this reference measurement to produce a difference value designated Z. At step 78, the microprocessor 34 checks to see if the absolute value of Z corresponds to a partial pressure which is greater than two millimeters of mercury. If this relationship is satisfied, recalibration is required and the program branches step 90.

As the breath rate increases, the fractional inspired carbon dioxide Fi $CO_2$ level increases. However, even at relatively high breathing rates, an excessively high value for the fractional inspired carbon dioxide indicates a need to recalibrate the hand-held monitor 10. Therefore, at step 80, a check is made whether the breath rate, as determined by the microprocessor 32, is less than twenty breaths per minute. If so, at step 82, a determination is made whether the fractional inspired carbon dioxide value is greater than six millimeters of mercury. If so, the offset calibration procedure is initiated by branching to step 90. If the breath rate is not less than twenty breaths per minute, the program execution advances to step 84 where a check is performed to see whether the breath rate is greater than forty breaths per minute. If so, the fractional inspired carbon dioxide measurement is inspected at step 86 to learn if it has a value greater than twenty millimeters of mercury. If such is the case, the offset calibration procedure at step 90 is initiated. Otherwise, when the breath rate is between twenty and forty breaths per minute, the program execution advances to step 88 to check whether the fractional inspired carbon dioxide level is greater than eight millimeters of mercury. Exceeding this threshold causes the offset calibration procedure to commence at step 90. Otherwise, there is no indication based on any of these parameters that offset recalibration is necessary and the routine ends returning to the point in the main control program at which the autocalibration routine was called.

The offset calibration procedure commences at step 90 in FIG. 3B at which the fifteen minute timer is reset to time another interval. Then the microprocessor 34 sends a command to the output driver 40 to change the position of valve 16 to direct ambient air through the $CO_2$ sensor 22 at step 91. A short delay occurs at this point to insure that ambient air has purged the patient's air from the sensor. Then the microprocessor 34 reads the output from the $CO_2$ sensor 22 to determine the carbon dioxide content of the ambient air at step 92 which measurement then is used to reset the value of the variable $CO_{2(ZERO)}$ at step 94. This resets the baseline of the graph in FIG. 2 against which the content of the carbon dioxide in the patient's breath is measured. This procedure automatically corrects the offset for the measurement process.

Next at step 95, the position of valve 16 is changed to send air from the patient to the $CO_2$ sensor 22. The fractional inspired carbon dioxide is measured during the next breath at step 96 using the value for $CO_{2(ZERO)}$, and the measurement stored at step 97 as the value of the variable designated Fi $CO_{2(BASE)}$. This completes the offset calibration procedure and the CAL FLAG is reset at step 98 before the program execution returns to the point in the main program from which the offset calibration routine was called.

I claim:

1. A method for calibrating a monitor which measures an amount of carbon dioxide in breath of an animal, steps of said method comprising:
   periodically measuring carbon dioxide content of air flowing into and out of the animal;
   producing an indication of a need for calibration of the monitor, in response to the carbon dioxide content of air flowing into or out of the animal;
   detecting when the animal is inhaling; and
   in response to the indication being produced, determining a measurement offset value for the monitor when the animal is inhaling.

2. The method as recited in claim 1 further comprising detecting when the animal is in apnea; and in response to the indication being produced, determining a new measurement offset value for the monitor when the animal is in apnea.

3. The method as recited in claim 1 wherein the step of determining a measurement offset value for the monitor comprises:
   measuring carbon dioxide content of ambient air surrounding the monitor; and
   defining a zero carbon dioxide reference level in response to the carbon dioxide content of ambient air which zero carbon dioxide reference level is employed subsequently by the monitor to measure carbon dioxide in air breathed by an animal.

4. The method as recited in claim 1 steps of which further comprising determining a new measurement offset value for the monitor in response to a predefined interval of time elapsing.

5. A method for calibrating a monitor which measures an amount of carbon dioxide in breath of an animal, steps of said method comprising:
   periodically sampling the breath of the animal to obtain measurements of fractional inspired carbon dioxide during a plurality of respiration cycles;
   averaging a plurality of fractional inspired carbon dioxide measurements to derive an average measurement;
   computing a difference between the average measurement and a reference fractional inspired carbon dioxide value; and
   changing a measurement offset of the monitor in response to the difference being greater than a predefined value.

6. The method as recited in claim 5 further comprising changing the reference fractional inspired carbon dioxide value to a measurement of fractional inspired carbon dioxide which is acquired during a respiration cycle of the animal following the step of changing the measurement offset of the monitor.

7. The method as recited in claim 5 wherein the step of changing a measurement offset of the monitor comprises:
   measuring carbon dioxide content of ambient air surrounding the monitor; and
   defining a zero carbon dioxide reference level in response to the carbon dioxide content of ambient air which zero carbon dioxide reference level is employed subsequently by the monitor to measure carbon dioxide in air breathed by an animal.

8. A method for calibrating a monitor which measures an amount of carbon dioxide in breath of an animal using a measurement offset, steps of said method comprising:
   periodically producing a measurement of the carbon dioxide content of the breath of the animal;
   producing a count of each occurrence when the measurement has a value that represents a negative partial pressure; and
   changing the measurement offset of the monitor in response to the count being greater than a predefined value.

9. The method as recited in claim 8 further comprising periodically decrementing the count.

10. The method as recited in claim 8 further comprising periodically decrementing the count at a rate that is at least one-tenth a rate at which the carbon dioxide content of air is periodically measured.

11. The method as recited in claim 8 wherein the step of changing a measurement offset of the monitor comprises:
    measuring carbon dioxide content of ambient air surrounding the monitor; and
    defining a zero carbon dioxide-reference level in response to the carbon dioxide content of ambient air which zero carbon dioxide reference level is employed subsequently by the monitor to measure carbon dioxide in the breath of the animal.

12. A method for calibrating a monitor which measures an amount of carbon dioxide in breath of an animal using a measurement offset, steps of said method comprising:
    periodically measuring carbon dioxide content of air flowing into and out of the animal;
    measuring a breath rate of the animal;
    determining from the breath rate whether the animal is in apnea;
    producing a count of each occurrence when the carbon dioxide content is above a given threshold level during apnea and;
    changing the measurement offset of the monitor in response to the count being greater than a predetermined value.

13. The method as recited in claim 12 further comprising periodically decrementing the count.

14. The method as recited in claim 12 further comprising periodically decrementing the count at a rate that is at least one-tenth a rate at which the carbon dioxide content of air is periodically measured.

15. The method as recited in claim 12 wherein the step of changing a measurement offset of the monitor comprises:
    measuring carbon dioxide content of ambient air surrounding the monitor; and
    defining a zero carbon dioxide reference level in response to the carbon dioxide content of ambient air which zero carbon dioxide reference level is employed subsequently by the monitor to measure carbon dioxide in the breath of the animal.

16. A method for calibrating a monitor which measures an amount of carbon dioxide in breath of an animal using a measurement offset, steps of said method comprising:
    measuring a breath rate of the animal;

measuring carbon dioxide content of air breathed by the animal to obtain a measurement of fractional inspired carbon dioxide;

determining whether the breath rate of the animal is below a first level;

determining when the measurement of fractional inspired carbon dioxide is greater than a first threshold value;

changing the measurement offset of the monitor in response to both the measurement of fractional inspired carbon dioxide being greater than the first threshold value and the breath rate of the animal being below the first level.

17. The method as recited in claim 16 further comprising:

determining whether the breath rate of the animal is below a second level which is greater than the first level;

determining when the measurement of fractional inspired carbon dioxide is greater than a second threshold value, which is greater than the first threshold value; and the step of changing the measurement offset of the monitor also is performed in response to the measurement of fractional inspired carbon dioxide being greater than the second threshold value when the breath rate of the animal is below the second level.

18. The method as recited in claim 17 further comprising:

determining whether the breath rate of the animal is between the first and second levels;

determining when the measurement of fractional inspired carbon dioxide is greater than a third threshold value which is between the first and second threshold values; and the step of changing the measurement offset of the monitor also is performed in response to the measurement of fractional inspired carbon dioxide being greater than the third threshold value when the breath rate of the animal is between the first and second levels.

19. The method as recited in claim 16 wherein the step of changing a measurement offset of the monitor comprises:

measuring carbon dioxide content of ambient air surrounding the monitor; and defining a zero carbon dioxide reference level in response to the carbon dioxide content of ambient air which zero carbon dioxide reference level is employed subsequently by the monitor to measure carbon dioxide in the breath of the animal.

20. A method for calibrating a monitor which measures an amount of carbon dioxide in breath of an animal using a measurement offset, steps of said method comprising:

periodically measuring a carbon dioxide content of the breath of the animal;

measuring a breath rate of the animal;

detecting, in response to the breath rate, when the animal is in apnea;

analyzing measurements of the carbon dioxide content to determine a level of fractional inspired carbon dioxide during a plurality of respiration cycles;

averaging a plurality of fractional inspired carbon dioxide measurements to derive an average measurement;

counting each carbon dioxide measurement having a negative partial pressure to produce a second count;

when the animal is in apnea, counting each occurrence of the carbon dioxide content being above a threshold level to produce a first count; and changing the measurement offset of the monitor when one of the following conditions occurs:
 (a) a difference between the average measurement and a reference fractional inspired carbon dioxide value exceeds a given value,
 (b) the second count is greater than a predefined value;
 (c) the first count is greater than a predetermined value; and
 (d) the level of fractional inspired carbon dioxide is greater than a predefined level when the breath rate of the animal is below a predetermined level.

21. The method as recited in claim 20 wherein the step of changing the measurement offset of the monitor comprises:

measuring carbon dioxide content of ambient air surrounding the monitor; and defining a zero carbon dioxide reference level in response to the carbon dioxide content of ambient air which zero carbon dioxide reference level is employed subsequently by the monitor to measure carbon dioxide in the breath of the animal.

* * * * *